United States Patent [19]

Malchman et al.

[11] 4,074,720

[45] Feb. 21, 1978

[54] CARDIAC PACER WITH RATE RUNAWAY PROTECTION

[75] Inventors: Franklin L. Malchman, King of Prussia; William J. Raddi, Philadelphia, both of Pa.; Susan Sharples, Cranbury, N.J.

[73] Assignee: ESB Incorporated, Philadelphia, Pa.

[21] Appl. No.: 674,380

[22] Filed: Apr. 7, 1976

[51] Int. Cl.² ............................................. A61N 1/36
[52] U.S. Cl. ............................................. 128/419 PG
[58] Field of Search ...... 128/419 PG, 419 R, 421–423

[56] References Cited

U.S. PATENT DOCUMENTS

| | | | |
|---|---|---|---|
| 3,253,596 | 5/1966 | Keller, Jr. | 128/419 PG |
| 3,460,542 | 8/1969 | Gemmer | 128/419 PG |
| 3,693,626 | 9/1972 | Cole | 128/419 PG |
| 3,903,897 | 9/1975 | Woollons et al. | 128/419 PG |
| 3,920,024 | 11/1975 | Bowers | 128/419 PG |
| 3,972,334 | 8/1976 | Wickham | 128/419 PG |

Primary Examiner—William E. Kamm
Attorney, Agent, or Firm—Gary V. Pack; Gilbert W. Rudman; Anthony J. Rossi

[57] ABSTRACT

A cardiac pacer having an improved oscillator circuit therein which provides rate runaway protection in the event of circuit malfunction. The oscillator establishes the normal operating rate of the pacer and limits the pacer operating rate to a predetermined rate which, while above the normal pacer operating rate, is still considered to be a safe pacer operating rate.

8 Claims, 8 Drawing Figures

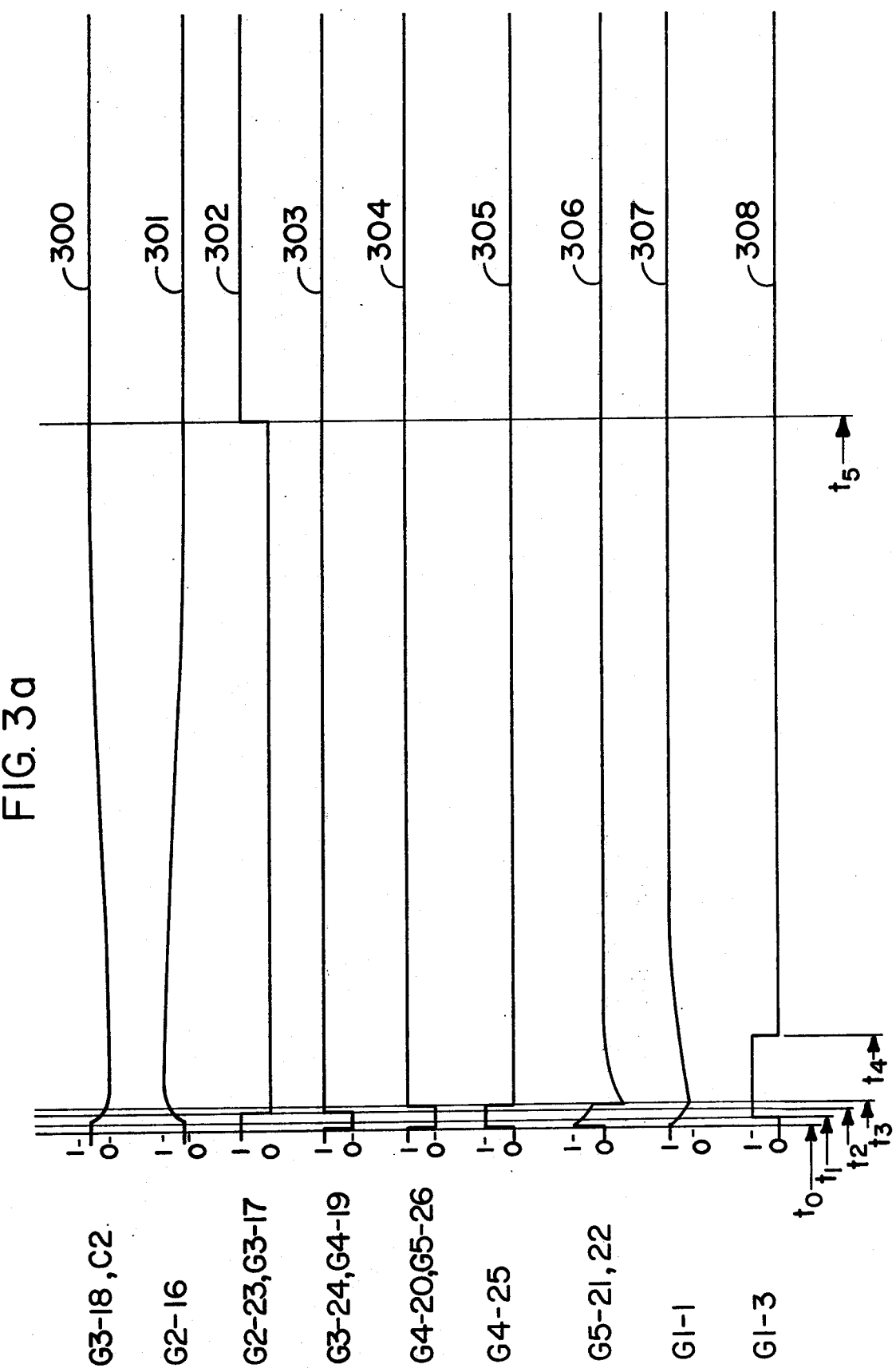

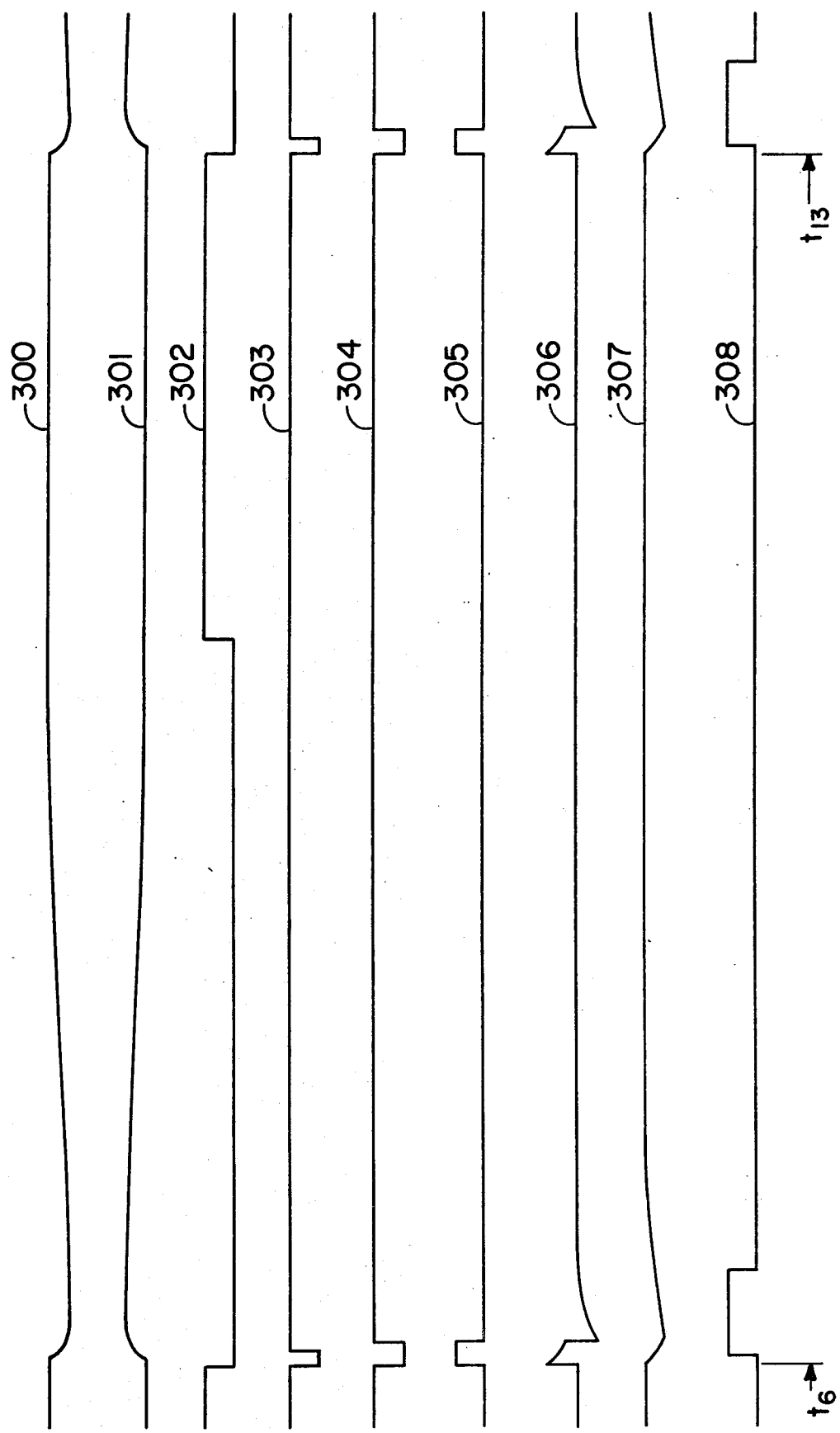

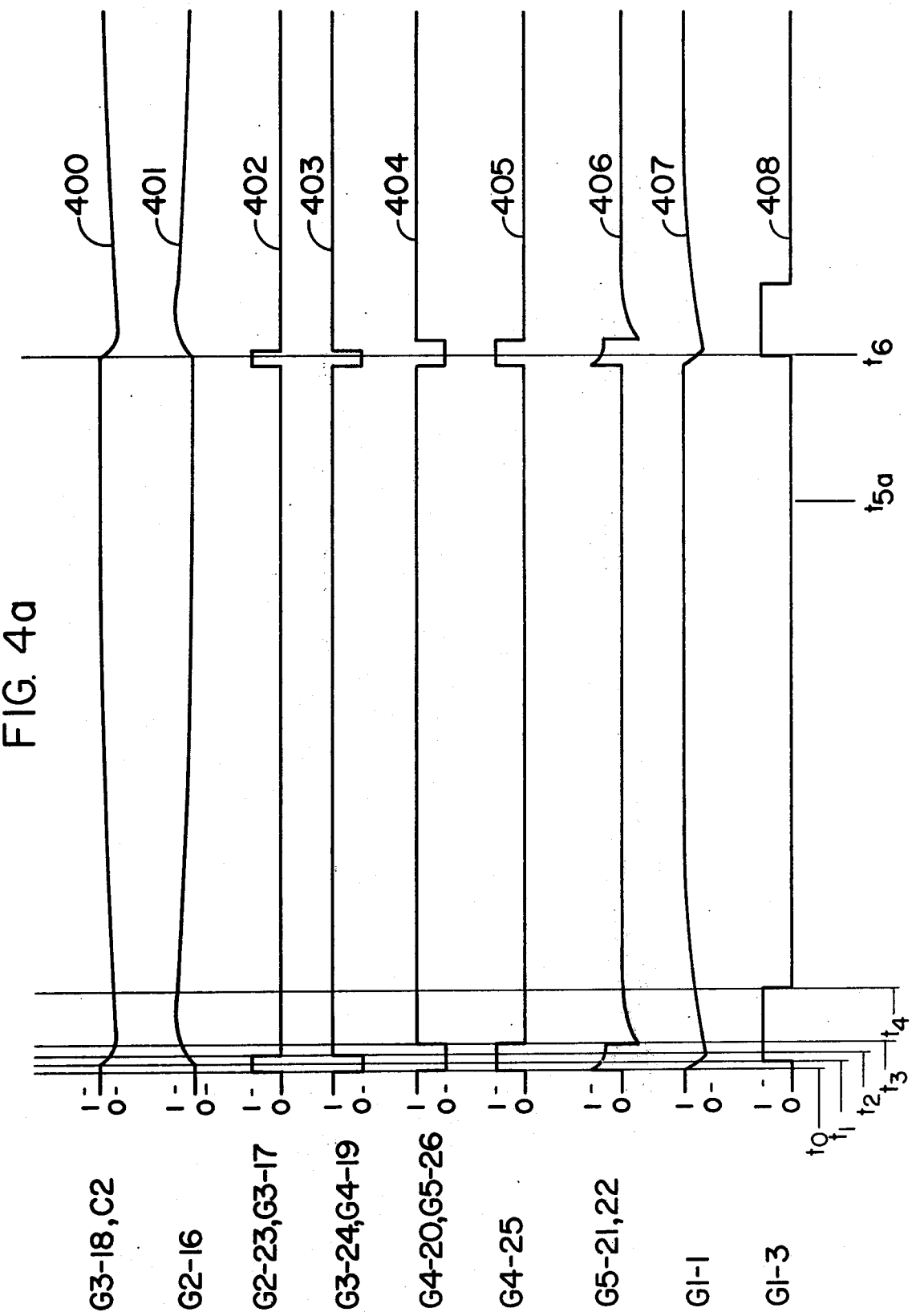

CARDIAC PACER WITH RATE RUNAWAY PROTECTION

BACKGROUND OF THE INVENTION

1. Field of the Invention

This invention relates to cardiac pacers and, more particularly, to improvements in oscillator circuits used in cardiac pacers. While the invention will be described in most detail in association with demand type pacers, the invention is applicable to all kinds of pacers having an oscillator circuit therein which establishes the normal operating rate of the pacer.

2. Description of the Prior Art

In electrical heart pacers and in particular demand type pacers, electrical stimulating pulses are delivered to the patient's heart only in the absence of natural heartbeats. Generally, the demand pacer is designed to deliver an electrical stimulating pulse to the heart at a predetermined time interval after the last natural heartbeat, and to continue to deliver stimulus pulses at a fixed rate as long as no natural heartbeats are sensed by the pacer. If a heartbeat is sensed by the pacer during the timing interval of the oscillator of the pacing device, the pacer oscillator is reset so that it starts its timing cycle over again and the pacer output is inhibited so that no stimulus pulse is delivered to the heart. The time interval between the moment when the pacer oscillator is reset and the time when it completes a timing cycle is sometimes referred to as the escape interval.

Such demand type pacers are well-known, have been miniaturized, are usually self-contained and powered by battery and are now wholly implanted within the body. It will therefore be appreciated that the packing density of circuit components in such a pacer is very high resulting in conditions which could lead to circuit malfunctions as, for example, malfunctions caused by current leakage between adjacent components or leads interconnecting components. In the past, such circuit malfunctions have caused pacers to fail in a manner resulting in a rate runaway condition which is clearly undesirable for the patient. In fact, it could be lethal.

Accordingly, a primary object of the present invention is to provide in a cardiac pacer a means for limiting the pacer operating rate to a predetermined rate which, while above the normal pacer operating rate, is still considered to be a safe pacer operating rate.

SUMMARY OF THE INVENTION

In accordance with the invention, an oscillator circuit is provided capable of use with a cardiac pacer. The oscillator includes a pulse generating network, a pulse rate network and a strobe network. The pulse generating network generates pulses at a first rate or at a second rate, the second rate being higher than the first rate. The pulse rate network, including pulse rate control means, establishes the rate at which the pulse generating network generates pulses with the pulse rate control means being normally operative to cause the pulse generating network to generate pulses at the first rate but, when the first rate exceeds the second rate, to cause the pulse generating network to generate pulses at the second rate. The strobe network establishes the beginning of each cycle of the pulse rate network.

A more complete understanding of the invention will be had from the following detailed description taken in connection with the accompanying drawings which form a part of this specification.

BRIEF DESCRIPTION OF THE DRAWINGS

FIGS. 3a, 3b, 4a, 4b and 5 show timing diagrams useful to explain the operation of the circuit of FIG. 2. FIGS. 3a and 3b for ease of illustration have been presented as two separate sheets of drawings which can be interconnected along a break line for viewing as a single drawing, the same being true for FIGS. 4a and 4b.

DESCRIPTION OF THE PREFERRED EMBODIMENT

In order to lay a foundation for the detailed description, which follows hereinafter, of the operation of the oscillator of the invention shown in FIG. 2, a brief description of the demand pacer illustrated in FIG. 1 will first be given. This will be followed by a general description of the component functions and circuit operation of FIG. 2 with the specific functions of the components and circuit operation of FIG. 2 becoming more evident in the detailed description of the operation of the oscillator circuit of FIG. 2.

Figures 1, 1A:
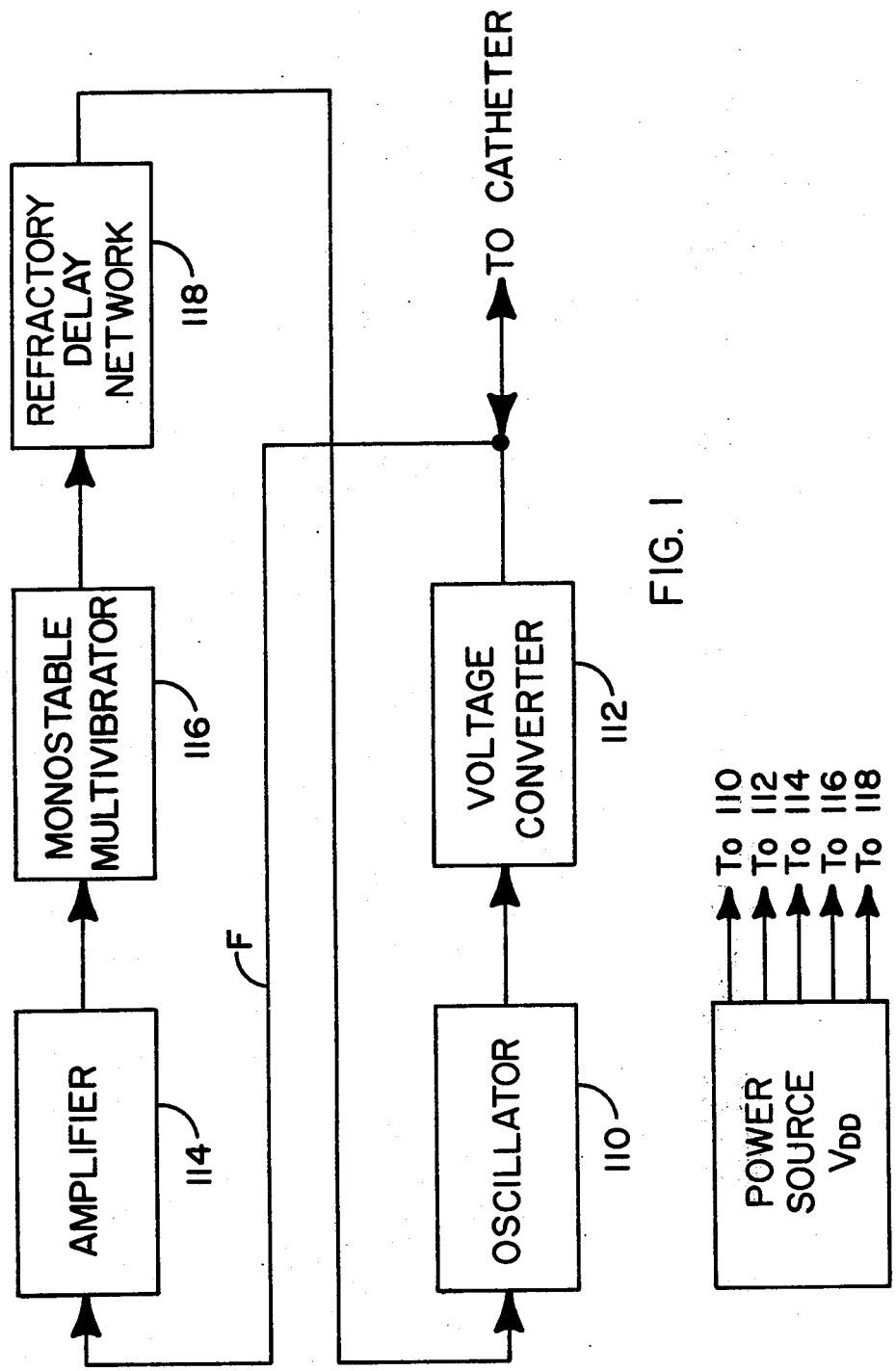
FIG. 1 is a block circuit diagram of a demand cardiac pacer embodying the invention.
FIG. 1a illustrates in block form the battery power source for the pacer of FIG. 1.

Brief Description of Demand Pacer of FIG. 1

As stated above, a demand pacer supplies a stimulating pulse to the heart whenever the time interval from the last heartbeat exceeds a predetermined interval, i.e., the escape interval. Otherwise, the heartbeat signal sensed by the pacer inhibits the generation of an output stimulating pulse and recycles the timing or rate network of the oscillator contained in the pacer that determines the time interval between stimulating pulses, i.e., resets the oscillator to begin a new cycle. Actually, the largest magnitude electrical signal generated by the heart activity is the QRS complex of the electrogram which corresponds to ventricular contraction, and it is the R-wave portion of this complex that is normally sensed by the demand pacer. The predetermined time or escape interval referred to is chosen to be slightly longer than the time interval naturally occurring between R-waves.

The block diagram of FIG. 1 shows the basic features of such a demand pacer. For ease of illustration, the power source $V_{DD}$ for the pacer shown in FIG. 1 is illustrated in FIG. 1a. The oscillator 110 and voltage converter 112 in the absence of the other blocks shown in FIG. 1 comprise a basic fixed rate or asynchronous pacer. The oscillator 110 provides a sequence of pulses on the order of 1ms in width at a nominal rate of 72 beats per minute corresponding to a time interval of 833 ms between pulses. Actually, pulse widths and rate are selected by design according to medical requirements and the numbers given are only by way of example. This is also true throughout this specification wherein typical or nominal values are indicated. It being understood that such typical or nominal values are given only by way of example.

The voltage converter 112 amplifies the voltage of the pulses to that required to properly stimulate the heart. The stimulating output pulses from the pacer are transmitted to the heart via a catheter (not shown), a flexible conductor insulated along its entire length except for a small portion at the end thereof which is lodged in the ventricle of the heart.

The addition of the amplifier 114, monostable multivibrator 116, and refractory delay network 118 converts the fixed rate pacer comprised of oscillator 110 and voltage converter 112 to a demand type pacer. In operation, the amplifier 114 senses the R-wave via the catheter and feedback path F and amplifies the signal to a level sufficient to trip the monostable multivibrator 116. The latter, in turn, activates the refractory delay network 118 and also resets the oscillator 110 to begin a new timing cycle. The refractory delay network 118, during its operative period, which is typically on the order of 250ms, blocks any other sensed signals such as those originating from electrical noise external to the body or from the T-wave in the electrogram complex from resetting the oscillator 110. Note that the amplifier 114 also senses the delivered stimulating pulse via the feedback path F. In providing a pulse, the oscillator 110 resets itself, so that the recycling action of the amplifier 114 and the refractory network 118 is redundant in this case. However, the refractory delay network 118 is activated and as before, prevents a second resetting of the oscillator 110 timing for 250ms following an output pulse from the voltage converter 112. A demand pacer of this type is disclosed in U.S. Pat. No. 3,759,266 issued on Sept. 18, 1973.

General Description of Oscillator 110

In the following description, various logic circuit elements are referred to and prior to describing the general operation of oscillator 110, the characteristics of such logic elements will be briefly set forth. Generally, ground states represent logical zeroes and voltage levels represent logical ones on the various terminals of logic circuit elements. Logic CMOS NAND gates are well known in the art. A truth table for a CMOS NAND gate is:

| Inputs | | Output |
|---|---|---|
| A | B | C |
| 0 | 0 | 1 |
| 0 | 1 | 1 |
| 1 | 0 | 1 |
| 1 | 1 | 0 |

It is seen that if either or both input terminals is at logic 0 (low), the output terminal signal is a logic 1 (high). Only when both input terminals are high does the output terminal go low. The concept of threshold is also used in describing the action of CMOS NAND gates. A given input terminal has a negative threshold and a positive threshold. For the CMOS NAND gates they are generally nearly equal in magnitude. Accordingly, when a signal of increasing voltage (such as may appear across a charging capacitor), is applied to an input terminal of a CMOS NAND gate and crosses the positive threshold of this input, the signal is then assumed to have undergone a transition from a logic 0 to a logic 1 insofar as the effects on the gate operation are concerned. When a signal of decreasing amplitude is applied to an input terminal of a CMOS NAND gate and crosses the negative threshold of this input terminal, the signal is assumed to have undergone a transition from a logic 1 to a logic 0.

CMOS semiconductor switches (analog gates) (illustrated in FIG. 2) S1, S2, and S3 are used to discharge the oscillator 110 timing capacitors C2 and C3. A low logic level at their input terminals, S1-4, S2-7, or S3-12 turns them off. That is the resistance of the path S1-5 to S1-6, or S2-8 to S2-9, or S3-13 to S3-14 is on the order of at least 100 megohms. A high logic level at their input terminals turns them on. Then each path resistance becomes about 1000 ohms.

Figure 2:
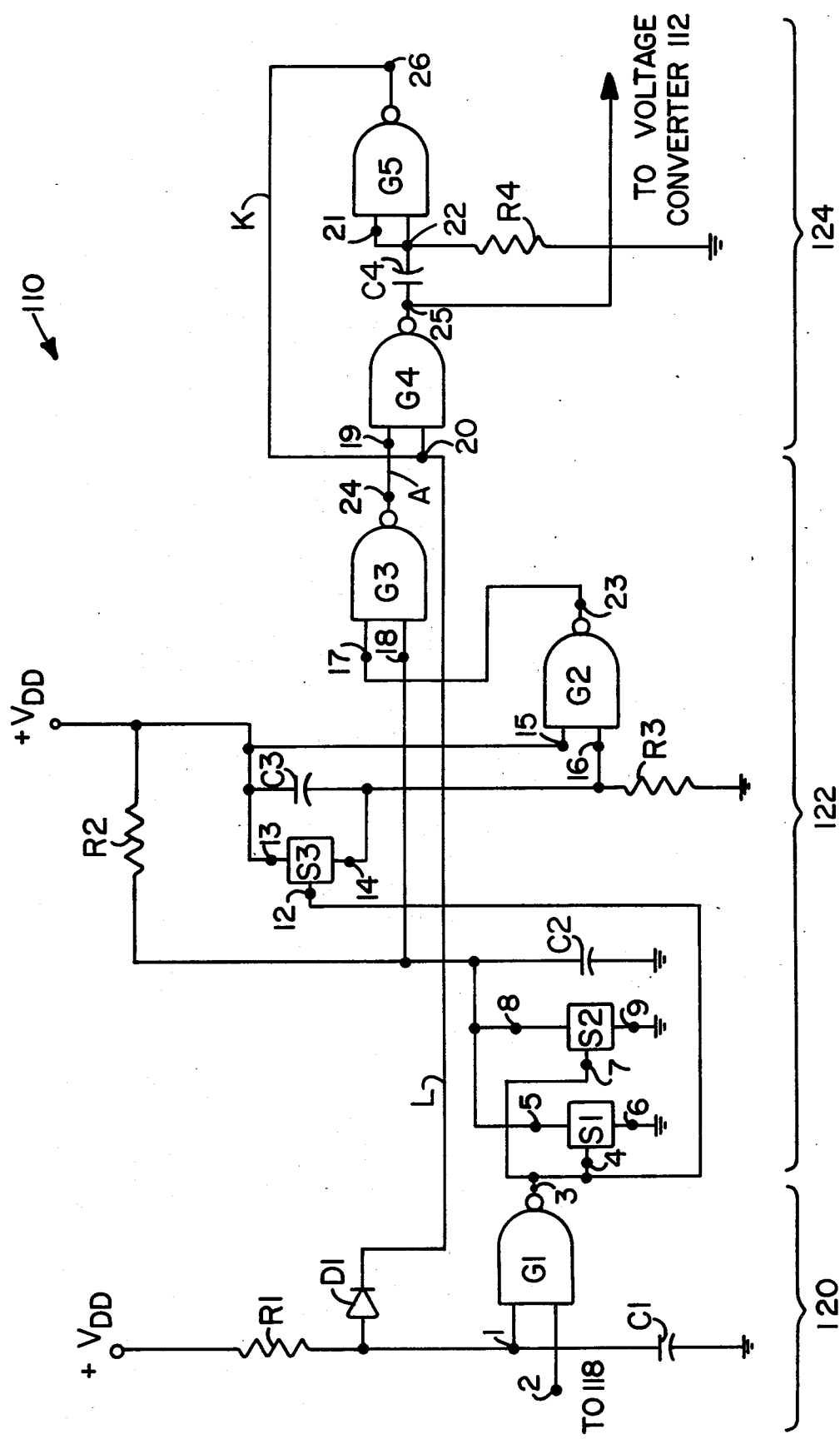
FIG. 2 is a schematic circuit diagram of an oscillator circuit in accordance with the invention.

Referring now to FIG. 2, oscillator 110 is that portion of the pacer shown in FIG. 1 which is the concern of the present invention. The oscillator 110 comprises a strobe network shown generally at 120, a pulse rate network shown generally at 122 and a monostable multivibrator or pulse generating network shown generally at 124.

The strobe network 120 comprises a means for establishing the beginning of each cycle of the pulse rate network 122. The strobe network 120 resets the timing cycle of the oscillator 110 by causing the simultaneous discharge of timing capacitors C2 and C3 in the pulse rate network 122. The pulse rate network 122 comprises means for establishing the time interval between or the rate of generation of output pulses from the pulse generating network 124. The pulse generating network 124 comprises means for generating pulses of predetermined width which are to be subsequently voltage amplified by the voltage converter 112, the width of the pulses remaining the same, and means for activating the strobe network for resetting the timing cycle of the oscillator 110.

The basic or normal pacer operating rate is set by the charging of capacitor C2 through resistor R2 until the voltage across the capacitor C2 reaches the threshold of logic gate G3 at its input terminal 18. Rate runaway protection, which is the concern of the present invention, is provided by the charging of capacitor C3 through resistor R3 until the voltage across capacitor C3 reaches the threshold of logic gate G2 at its input terminal 16; the gate G2 then activates and the output thereof, appearing on output terminal 23, is applied to the input terminal 17 of gate G3 to enable gate G3. Both input terminals 17 and 18 must have applied thereto the same high logic level signals in order to activate gate G3 and when this occurs, the signal on output terminal 24 of gate G3 activates the pulse generating network 124 comprising gates G4 and G5 via input terminal 19 of gate G4. An output of the pulse generating network 124, which is fed to the voltage converter 112, appears on the output terminal 25 of gate G4. The output pulse appearing on output terminal 25 (normally at ground level) is typically a 1ms wide positive pulse. Another output of the pulse generating network 124 appears simultaneously with the one appearing on terminal 25 at output terminal 26 of gate G5. This latter output is also typically a 1ms wide pulse, however, it is a negative pulse (normally at $V_{DD}$ level) and is applied via the feedback path K-L and diode D1 to activate the strobe network 120.

The strobe network 120 in turn, via the signal appearing on output terminal 3 of gate G1, turns on switches S1, S2 and S3, via input terminals 4, 7 and 12, respectively, for a sufficient length of time, nominally 3.5 ms, to essentially completely discharge capacitors C2 and C3. When the strobe network 120 deactivates, switches S1, S2 and S3 are turned off, thereby permitting capacitors C2 and C3 to begin charging again to start a new timing cycle, i.e., the oscillator 110 is reset.

Thus, the signal at input terminal 17 of gate G3 appears before that at input terminal 18. Since input terminals 17 and 18 must act together to activate gate G3 and subsequently the pulse generating network 124, the rate at which the pulse generating network 124 causes the delivery of an output pulse is thereby determined by the action of resistor R2 and capacitor C2.

From the foregoing it will be understood that the normal pacer operating rate, in the range of 60 to 100 beats per minute, is predetermined by the magnitude of capacitor C2 and resistor R2 which together establish the interval of time required for the voltage across capacitor C2 to reach the threshold of input terminal 18 of gate G3. Since time interval is the inverse of rate, a faster rate implies a shorter interval. In accordance with the invention, the magnitudes of capacitor C3 and resistor R3 are chosen such that the charging of capacitor C3 via resistor R3 is set for a faster rate (shorter interval), in the range of 110 to 150 beats per minute, nominally 120 beats per minute, than that set for capacitor C2 and resistor R2. The maximum safe pacer operating rate is considered by the medical profession to be 150 beats per minute with 180 beats per minute being considered possibly lethal. Therefore, while the pacer operating rate set for capacitor C3 and resistor R3 is above the normal pacer operating rate, it is still considered to be a safe pacer operating rate. It can thus be seen that resistor R2, capacitor C2 and resistor R3, capacitor C3 comprise pulse rate control means for pulse rate network 122.

At this point it should be explained that the packing density of circuit components in an implantable cardiac pacer is very high resulting in the possibility for a circuit malfunction to occur such that the rate of charging of capacitor C2 is increased and the interval of time required to reach the threshold of input terminal 18 is decreased. This would correspond to an increase in the normal pacer operating rate. In this circumstance, the signal at input terminal 18 can reach the threshold thereof before the signal at input terminal 17 appears, and thus, the rate of generation of output pulses by the pulse generating network 124 is limited to 120 beats per minute by the timing action of resistor R3 and capacitor C3.

A circuit malfunction that increases the charging rate of capacitor C2 can be caused by current leakage from an adjacent conductor run on a printed circuit board that would have the affect of reducing the value of resistor R2 which would tend to increase the charging rate of capacitor C2 and therefore increase the normal rate of oscillations of oscillator 110. A leakage path from a faulty gate, as for example gate G3 via input terminal 18, would cause terminal 18 to act as an output terminal feeding capacitor C2, or a leakage path from output terminals 5 and 8 of switches S1 and S2 would also cause them to act as output terminals feeding capacitor C2; the resulting affect would be for capacitor C2 to charge through a smaller value of resistance than resistor R2 causing an increase in the rate of oscillations of oscillator 110.

Alternatively, a malfunction in the timing circuit comprised of capacitor C3 and resistor R3 that would cause the signal to appear at input terminal 17 of gate G3 after a shorter interval of time than that corresponding to 120 beats per minute is of little consequence since the normal pacer operating rate of 72 beats per minute would still be set by the timing circuit comprised of resistor R2 and capacitor C2. Assuming independent events and a very low probability of failure for either of the timing circuits, the probability of both timing circuits failing at the same time is the product of the two probabilities. Thus, the likelihood of both timing circuits failing together is extremely remote.

Detailed Description of Oscillator 110

Considering the operation of oscillator 110 of FIG. 2 in greater detail, the sequence of circuit operations is shown in the timing diagrams illustrated in FIGS. 3a, 3b, 4a, 4b and 5. Referring now to FIGS. 3a and 3b, and starting first with a description of the pulse generating network 124 at time $t_o$, we assume input terminals 17 (line 302) and 18 (line 300) of gate G3 have gone high with a resultant low output on terminal 24 (line 303) of gate G3. The latter low signal level is coupled via conductor A to input terminal 19 (line 303) of gate G4. In its normal or quiescent state, the input terminal 20 (line 304) of gate G4, which is tied to output terminal 26 (line 304) of gate G5 via conductor K, is high as is input terminal 19 of gate G4. Therefore, output terminal 25 (line 305) of gate G4 is normally low. When input terminal 19 of gate G4 goes low, output terminal 25 of gate G4 goes high. Prior to time $t_o$, we assume the voltage across capacitor C4 is zero and since output terminal 25 of gate G4 is also zero, the voltage at input terminals 21 and 22 (line 306) of gate G5 is also zero or a logic zero. At time $t_o$, when output terminal 25 of gate G4 goes high, input terminals 21 and 22 of gate G5 instantaneously go high because the voltage across capacitor C4 remains zero at the initial instant. After the natural delay through the gate (about 0.5 microseconds) output terminal 26 of gate G4 goes low as does input terminal 20 of gate G4. Now capacitor C4 begins to charge from power source $V_{DD}$ the output resistance of gate G4 and resistor R4. When output terminal 25 of gate G4 went high, the current in resistor R4 jumped instantaneously to a high value determined essentially by power source $V_{DD}$ and resistor R4. As capacitor C4 charges, the voltage drop across capacitor C4 increases exponentially; the current through resistor R4 and the voltage across it diminish correspondingly. When the diminishing voltage across resistor R4 reaches the negative threshold of input terminals 21 and 22 of gate G5, output terminal 26 of gate G5 switches from low to high at time $t_3$. The time during which output terminal 26 of gate G5 remained low or the time during which output terminal 25 of gate G4 remained high is the width of the delivered output pulse fed to the voltage converter 112; this time is on the order of 1 millisecond. By circuit operation to be described below, the input terminal 19 of gate G4 remains low for a few brief microseconds before going high again at time $t_2$. Yet it remained low long enough for the low signal at input terminal 20 of gate G4 to become established. At time $t_3$, when input terminal 20 of gate G4 goes high, and since input terminal 19 of gate G4 is high, output terminal 25 of gate G4 returns to its normally low state.

Considering now the action of the strobe network 120, the input terminal 2 thereof is normally kept high by the operation of the refractory delay network 118. Input terminal 2 is caused to go low whenever an R-wave or an output pulse from the voltage converter 112 is sensed and fed back to the refractory delay network 118 via path F, amplifier 114 and monostable multivibrator 116. The sensing of either an R-wave or an output pulse from voltage converter 112 causes the refractory delay network 118 to drive input terminal 2 low resulting in a high signal on normally low output terminal 3 of gate G3. The significance of the action of the refractory delay network 118 on strobe network 120 will appear more fully hereinafter in the explanation of inhibited or demand pacer operation of the oscillator 110.

The negative going signal at time $t_o$ at output terminal 26 of gate G5 and terminal 20 of gate G4 is coupled via conductor L to diode D1. Prior to time $t_o$, capacitor C1 had been charged fully to the voltage of the power source $V_{DD}$ via resistor R1. With output terminal 26 of gate G5 low, capacitor C1 now begins to discharge toward ground through diode D1 and the output resistance of gate G5. When the diminishing voltage on capacitor C1 crosses the negative threshold of input terminal 1 (line 307) of gate G1, output terminal 3 (line 308) of gate G1 which had been prior to $t_o$ normally low, goes high at time $t_1$. This logic one level signal turns on switches S1, S2 and S3 via input terminals 4, 7, and 12 of switches S1, S2 and S3, respectively. Capacitor C2 (line 300) begins to discharge through the parallel combination of switches S1 and S2 and capacitor C3 through switch S3. Output terminal 3 of gate G1 has been designed to remain high long enough for capacitors C2 and C3 to become, for all practical purposes, completely discharged in time $t_4$-$t_1$, about 3.5 ms. This is insured by the recharging of capacitor C1 via resistor R1 after output terminal 26 of gate G5 and input terminal 20 of gate G4 return to logic one at time $t_3$. Diode D1 blocks current flow into the capacitor C1 through the output resistance of gate G5. When capacitor C1 voltage reaches the positive threshold of input terminal 1 of gate G1, output terminal 3 of gate G1 returns to logic 0 thereby turning off switches S1, S2 and S3 at time $t_4$.

As capacitor C3 discharges through switch S3, the increasing voltage across resistor R3 passes the positive threshold of input terminal 16 of gate G2 (line 301) resulting in a logic 0 at output terminal 23 of gate G2 and input terminal 17 of gate G3. As capacitor C2 discharges, the diminishing voltage across it passes the negative threshold of input terminal 18 of gate G3. Either of the foregoing events is sufficient to cause output terminal 24 of gate G3 to return to its normal logic 1 state at time $t_2$.

Considering now the normal oscillator 110 timing operation, at time $t_4$ capacitor C2 begins to charge towards source voltage $V_{DD}$ via resistor R2 and capacitor C3 charges toward ground via resistor R3. When the diminishing voltage across resistor R3 reaches the negative threshold of input terminal 16 of gate G2, output terminal 23 of gate G2 and hence input terminal 17 of gate G3 switches from a normally low state to a logic 1 at time $t_5$ since input terminal 15 of gate G2 is tied permanently high. When the voltage across capacitor C2 reaches the positive threshold at input terminal 18 of gate G3, gate G3 now has two input terminals, at time $t_6$, at logic 1 and therefore, output terminal 24 of gate G3 switches low. Thus a new timing cycle begins with time $t_6$ considered to be a new time $t_o$. Note that input terminal 17 of gate G3 reaches a logic 1 level before input terminal 18 of G3 because the timing action of capacitor C3 and resistor R3 has been designed for a period of 500 ms (120 beats per minute) as compared to the timing action of capacitor C2 and resistor R2 which is normally designed for periods ranging from 1000 ms to 600 ms depending upon the normal pacer operating rate desired. Since the input terminal 17 of gate G3 waits for input terminal 18 of gate G3 to reach a logic 1, normal pacer operating rate is controlled by the timing action of capacitor C2 and resistor R2.

While the operation of the oscillator 110 will not be described with respect to the remainder of the timing diagrams shown in FIGS. 3a and 3b, the operating steps are shown in the timing diagram and may be readily understood with reference to the detailed explanation just given noting that time $t_6$ is to be considered a new time $t_o$ and that the time interval between time $t_6$ and time $t_{13}$ are equal.

Figure 4B:
Figure 5:
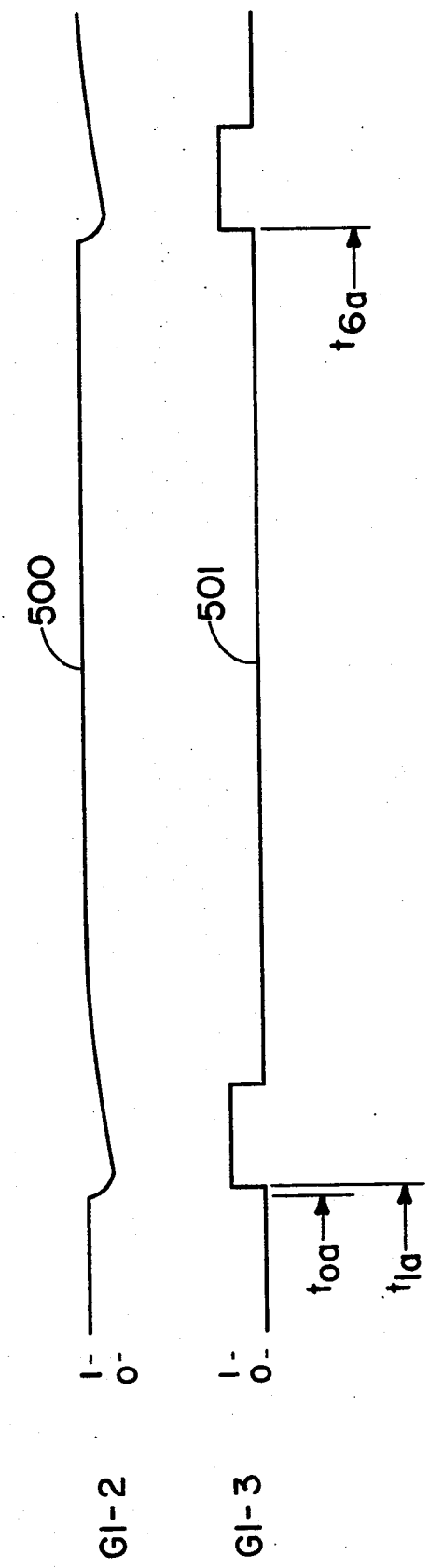

Referring now to FIGS. 4a and 4b wherein except for line 402, lines 400-408 correspond to lines 300-308 of FIGS. 3a and 3b, a condition will now be described wherein a circuit malfunction has occurred resulting in a speed up of the timing action of capacitor C2 and resistor R2. Under such circumstances, input terminal 18 of gate G3 can reach a logic 1 level before that of input terminal 17 of gate G3 as is shown at time $t_{5a}$ in FIG. 4a. However, after output terminal 23 of gate G2 becomes high, both inputs of gate G3 are now high and the same sequence of events as described above with reference to FIGS. 3a and 3b beginning a time $t_o$ takes place. Note that output terminal 23 of gate G2 remains high for only a short interval as contrasted with the situation in FIGS. 3a and 3b where it remained high for the length of time required for the timing action of capacitor C2 and resistor R2 to catch up. In this situation, the pacer timing rate is controlled by the timing action of capacitor C3 and resistor R3, the rate runaway protection network of the invention, and thus the pacer operating rate is limited to a safe 120 beats per minute.

The operation of the oscillator 110 just given essentially covered the situation of fixed rate operation. Referring now to the timing diagram shown in FIG. 5, which only illustrates the conditions of terminals 2 and 3 of gate G1 of the strobe network 120; line 500 also indicates the rate of occurrence of an R-wave in rate (not shape). During demand pacer operation, the strobe network 120 operates in a similar manner via input terminals 1 and 2 of gate G1 to cause capacitors C2 and C3 to discharge prior to their charging to voltages which would otherwise pass the thresholds at input terminal 18 of gate G3 and input terminal 16 of gate G2 thereby initiating a new rate timing cycle and preventing the generation of an output pulse from pulse generating network 124.

Stated another way, each time an R-wave is sensed and processed through the refractory delay network 118, input terminal 2 (line 500) of gate G1 goes low resulting in a high level signal on output terminal 3 (line 501) of gate G1 which in turn effects operation of switches S1, S2 and S3 which cause capacitors C2 and C3 to discharge before their respective voltages can reach the threshold level of the levels on input terminal 18 of gate G3 and input terminal 16 of gate G2. Thus, the high level signals at output terminal 23 of gate G2 and input terminal 17 of gate G3 would be terminated at time $t_{6a}$ (prior to the time $t_6$ of FIGS. 3a and 3b). The waveforms on lines 303, 304, 305, 306 and 307, of FIG. 3 therefore never develop. Accordingly, in demand pacer operation, the rate of occurrence of the high level signal on terminal 3 (line 501) of gate G3 and its effects depends on the rate of occurrence of the sensed R-wave, causing, through the operation of the refractory delay network 118, input terminal 2 (line 500) of gate G1 to go low.

Examples of components illustrated in FIG. 2 are set forth in the table below:

| Component | | Commercial Type |
|---|---|---|
| Gates: | G1, G2, G3, G4 and G5 | Schmitt Trigger, or ¼ RCA CD4011 Quad NAND gate |
| Switches: | S1, S2, S3 | Each, ¼ RCA CD4066A Quad Bilateral Switch |
| Diode: | D1 | IN914 |
| Resistor: | R1 | About 3.0 meg. ohms |
| Resistor: | R2 | About 600 K ohms |
| Resistor: | R3 | About 6.0 meg. ohms |
| Resistor: | R4 | About 420 K ohms |
| Capacitor: | C1 and C4 | 1500 pico farads |
| Capacitor: | C2 | 1.0 micro farads |
| Capacitor: | C3 | 0.12 micro farads |

Having thus described our invention, we claim:

1. An oscillator system suitable for use with a cardiac pacer system, said oscillator system designed so that in the event its primary rate control system accelerates out of control, a secondary rate control system prevents the oscillator from producing signals at a rate greater than a predetermined high rate controlled by the secondary rate control system, said oscillator system comprising:
   (a) cycle initiation means responsive to the output from said oscillator system for producing a timing initiation signal;
   (b) primary timing circuit means, responsive to the timing initiation signal, for producing a first rate control signal a predetermined time period after receipt of the timing initiation signal;
   (c) secondary timing circuit means, responsive to the timing initiation signal, for producing a second rate control signal a predetermined time period after receipt of the timing initiation signal, said predetermined time period normally being less than the predetermined time period for the primary rate control means;
   (d) first gate means, responsive to the second rate control signal, for producing an output signal;
   (e) second gate means, responsive to the first rate control signal and an output signal from the first gate means, for producing a command signal only upon receipt of both the control signal and said output signal; and
   (f) means, responsive to the command signal from the second gate means, for producing an oscillator system output signal with a predetermined width, whereby rate runaway protection is provided because the maximum rate obtainable is restricted by the secondary timing circuit means in the event the primary timing circuit means fails to function properly and produces a first rate control signal before the second rate control signal is produced by the secondary timing circuit means.

2. The oscillator system recited in claim 1, wherein the first gate means and the second gate means are each logical NAND gates.

3. The oscillator system recited in claim 1, wherein the cycle initiation means comprises logical gating means for producing the timing initiation signal for activating the primary and secondary timing circuit means in response to the oscillator system output pulse.

4. The oscillator system recited in claim 3, wherein the logical gating means of the cycle initiation means is also responsive to an external pulse indicative of a patient's heartbeat, to eliminate the timing initiation signal, thereby terminating the timing cycles of the primary and secondary timing circuit means before rate control signals are produced.

5. The oscillator system recited in claim 4, wherein the timing initiation signal is produced by the logical gating means of the cycle initiation means at all times except during the time the oscillator system output pulse is produced, whereby the primary and secondary timing circuits are reset at the beginning of the oscillator system output pulse and the timing process begins upon termination of said output pulse.

6. The oscillator system recited in claim 5, wherein the primary timing circuit means comprises a first timing capacitor connected in series with a first resistance means, and first control means for permitting said first capacitor to be charged only in response to the timing initiation signal; and wherein the secondary timing circuit means comprises a second timing capacitor connected in series with a second resistance means, and second control means for permitting said second capacitor to be charged only in response to the timing initiation signal.

7. The oscillator system recited in claim 6, further comprising first means for connecting the primary timing circuit to said second gate means so that in the event the first capacitor becomes open circuited, said second gate means remains operative in response to its other input signal.

8. The oscillator system recited in claim 6, further comprising second means for connecting the secondary timing circuit to said first gate means so that in the event the second capacitor becomes open circuited, said first gate means continuously produces the command signal, whereby the second gate means remains operative in response to its other input signal.

* * * * *